(12) United States Patent
Bauer et al.

(10) Patent No.: US 7,220,791 B2
(45) Date of Patent: May 22, 2007

(54) STYRENE-HYPOPHOSPHITE ADDUCT, A PROCESS FOR PREPARATION THEREOF, AND ITS USE

(75) Inventors: Harald Bauer, Kerpen (DE); Sebastian Hoerold, Diedorf (DE); Werner Krause, Huerth (DE); Martin Sicken, Cologne (DE); Peter Staniek, Binzen (DE)

(73) Assignee: Clariant produkte (Deutschland) GmbH, Sulzbach (DE)

( * ) Notice: Subject to any disclaimer, the term of this patent is extended or adjusted under 35 U.S.C. 154(b) by 429 days.

(21) Appl. No.: 10/854,606

(22) Filed: May 26, 2004

(65) Prior Publication Data

US 2004/0242738 A1 Dec. 2, 2004

(30) Foreign Application Priority Data

May 30, 2003 (DE) .............................. 103 24 568

(51) Int. Cl.
*C08K 5/51* (2006.01)
(52) U.S. Cl. .................. 524/147; 252/609; 524/99; 524/100
(58) Field of Classification Search ............. 524/133, 524/147, 99–100; 252/609
See application file for complete search history.

(56) References Cited

U.S. PATENT DOCUMENTS

| | | | |
|---|---|---|---|
| 3,926,821 A | 12/1975 | LeSuer | |
| 4,740,332 A | 4/1988 | Thottathil | |
| 5,326,805 A | 7/1994 | Sicken et al. | |
| 6,355,832 B1 | 3/2002 | Weferling et al. | |
| 6,365,071 B1 | 4/2002 | Jenewein et al. | |
| 6,534,673 B1 | 3/2003 | Weferling et al. | |
| 6,547,992 B1 | 4/2003 | Schlosser et al. | |

FOREIGN PATENT DOCUMENTS

| | | |
|---|---|---|
| DE | 19614424 | 10/1997 |
| DE | 19752735 | 7/1999 |
| DE | 19851729 | 5/2000 |
| DE | 19960671 | 9/2000 |
| DE | 19920276 | 11/2000 |
| EP | 05844567 | 3/1994 |
| SU | 1077896 | * 3/1984 |
| WO | WO 97/39053 | 10/1997 |

OTHER PUBLICATIONS

EPO Search Report for EP04012049, mailed Mar. 2, 2005.
Fu, Xiang Kai et al., "Preparation of Polystyrenylphosphonous Acid of Low Polymerization Degree & Influence of Initiators upon Free Radical Reaction Mechanism" Chinese Chemical Letters vol. 13, No. 3, pp. 219-222; (2002).
Devedjiev et al., "On the Interaction Between Hypophosphorous Acid & Alcohols," Phosphorus & Sulfur. 1 pp. 7-11 (1987).
DIN 53 916 (Edition Aug. 1975).
Deprele et al., "Triethylborane-Initiated Room Temperature Radical Addition of Hypophosphites to Olefins: Synthesis of Monosubstituted Phosphinic Acids and Esters," Journal of Org. Chem. vol. 66 pp. 6745-6755(2001).
Fu et al., "Preparation of Polystrenylphosphonous Acid of Low Polymerization Degree and Influence of Initiators Upon the Free Radical Reaction Mechanism," Chinese Chemical Letters, vol. 13, No. 3, pp. 219-222(2002).
German Office Action for DE 10324568.5, mailed Feb. 10, 2004.

* cited by examiner

*Primary Examiner*—Peter Szekely
(74) *Attorney, Agent, or Firm*—Richard P. Silverman

(57) ABSTRACT

The invention relates to a styrene-hypophosphite adduct of the formula (I)

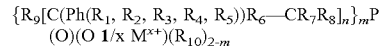

where
$R_1$, $R_2$, $R_3$, $R_4$, $R_5$, $R_6$, $R_7$ and $R_8$ are identical or different and are hydrogen, alkyl, linear or branched, aryl, aralkyl, oxoalkyl, oxoaryl, aminoalkyl, and/or aminoaryl,
$R_9$ is H or a free-radical-initiator radical,
$R_{10}$ is H,
$M^{x+}$ is Li, Na, K, Mg, Ca, Sr, Ba, Al, Ge, Sn, Bi, Sb, Pb, Ti, TiO, Zr, ZrO, Zn, Fe, Ce, Mn, and/or a protonated nitrogen base having the valency x,
m=1 or 2, and
n=from 1 to 100, and is the number of styrene units $C(Ph(R_1, R_2, R_3, R_4, R_5))R_6$—$CR_7R_8$ inserted into the P—H bond.

35 Claims, No Drawings

STYRENE-HYPOPHOSPHITE ADDUCT, A PROCESS FOR PREPARATION THEREOF, AND ITS USE

The present invention relates to a styrene-hypophosphite adduct, to a process for the preparation thereof, and to its use.

Fu, Yan, and Chen describe (Fu, Xiang Kai; Yan, Sui; Chen Li. Chinese Chemical Letters 2002, 13(3), 219–222) the preparation of an oligomeric product of an addition reaction between styrene and sodium hypophosphite. This utilizes the reactivity of a P—H function in the hypophosphite and inserts styrene units into the P—H bond, in a free-radical-initiated addition reaction. Up to 4 styrene units may be inserted. The phosphorus-containing end group takes the form of a free phosphonous acid. Ethanol is used as solvent. Concentrated sulfuric acid is added in order to obtain the phosphonic acid directly.

A disadvantage here is that sulfuric esters can be formed as by-products, in considerable amounts.

Another disadvantage is that the phosphorus yields resulting during the synthesis are below 10%. A further disadvantage is that the resultant product comprises considerable proportions of free-radical initiator incorporated by the reaction—from 18 to 41% by weight in the case of azobisisobutyronitrile (AIBN) as free-radical initiator.

U.S. Pat. No. 4,740,332 describes the preparation of 4-phenylbutylphosphonous acid, the solvent used comprising ethanol with concentrated sulfuric acid, and the initiator used comprising azobisisobutyronitrile.

Devedjiev, Ganev, Stevanova and Borisov (I Devedjiev, V Ganev, R Stevanova, G Borisov, On the interaction between hypophosphorus acid and alcohols, Phosphorus and Sulfur, 31(1987)7–11) describe the decomposition of hypophosphorous acid during its reaction with (short-chain) alcohols. This decomposition reaction may be a reason for the low phosphorus yield described by Fu et al. Polystyrene-based plastics are usually equipped with halogen-based flame retardants. Antimony oxide is sometimes used as synergist. A disadvantage here is that antimony-containing and/or halogen-containing gases can be evolved in the event of a fire.

It was therefore an object to eliminate the disadvantages of the prior art for preparing the styrene-hypophosphite adduct in relation to the low phosphorus yields. Furthermore, the proportion of initiator incorporated during the reaction should be reduced.

The preparation should moreover omit any use of ethanol, which is combustible and is the source of by-products.

The inventive product has high phosphorus content.

Surprisingly, it was moreover found that the inventive styrene-hypophosphite adduct can be used in a halogen- and antimony-free flame retardant for vinyl polymers (polystyrene-based polymers).

Surprisingly, it was moreover found that the inventive styrene-hypophosphite adduct effectively reduces the concentration of monomeric styrene in the polymer.

The invention therefore provides a styrene-hypophosphite adduct of the formula (I)

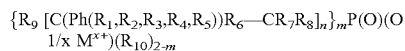

where
$R_1$, $R_2$, $R_3$, $R_4$, $R_5$, $R_6$, $R_7$ and $R_8$ are identical or different and are hydrogen, alkyl, linear or branched, aryl, aralkyl, oxoalkyl, oxoaryl, aminoalkyl, and/or aminoaryl, $R_9$ is H or a free-radical initiator radical,
$R_{10}$ is H,
$M^{x+}$ is Li, Na, K, Mg, Ca, Sr, Ba, Al, Ge, Sn, Bi, Sb, Pb, Ti, TiO, Zr, ZrO, Zn, Fe, Ce, Mn, and/or a protonated nitrogen base having the valency x,
m=1 or 2, and
n=from 1 to 100, and is the number of styrene units C(Ph($R_1$, $R_2$, $R_3$, $R_4$, $R_5$))$R_6$—CR_7R_8$ inserted into the P—H bond.

The arrangement of the monomers in the (C(Ph($R_1$, $R_2$, $R_3$, $R_4$, $R_5$))$R_6$ CR_7R_8$)_n$ chain is preferably random, but any of the other isotactic, atactic, or syndiotactic configurations is also in accordance with the invention.

$R_1$, $R_2$, $R_3$, $R_4$, $R_5$, $R_6$, $R_7$ and $R_8$ are preferably identical or different, and are preferably hydrogen; methyl, ethyl, n-propyl, n-butyl, n-pentyl; isopropyl, isobutyl, tert-butyl, neopentyl; phenyl; hydroxy, methoxy, ethoxy, propoxy, butoxy, phenoxy; amino, methylamino, ethylamino, propylamino, butylamino, N,N-dimethylamino, diethylamino, dipropylamino, or dibutylamino, and n is from 1 to 10.

$R_1$, $R_2$, $R_3$, $R_4$, $R_5$, $R_6$, $R_7$ and $R_8$ are particularly preferably identical or different, and are particularly preferably hydrogen and/or methyl.

The phosphorus content of the styrene-hypophosphite adduct is preferably from 8 to 25% by weight.

The phosphorus content of the styrene-hypophosphite adduct is particularly preferably from 11 to 20% by weight.

The phosphorus content of the aluminum salt of the styrene-hypophosphite adduct is preferably from 8 to 25% by weight.

The phosphorus content of the aluminum salt of the styrene-hypophosphite adduct is particularly preferably from 11 to 20% by weight.

The phosphorus content of the zinc salt of the styrene-hypophosphite adduct is preferably from 6 to 20% by weight.

The phosphorus content of the zinc salt of the styrene-hypophosphite adduct is particularly preferably from 7.5 to 17.5% by weight.

The particle size of the styrene-hypophosphite adduct is preferably from 0.1 to 1000 µm, the proportion of the $R_9$ side chains deriving from the initiator is preferably below 40%, and the styrene binding power is preferably from 260 to 810 mg of styrene/g.

The particle size of the styrene-hypophosphite adduct is particularly preferably from 10 to 100 µm, the proportion of the $R_9$ side chains deriving from the initiator is particularly preferably below 18%, and the styrene binding power is particularly preferably from 360 to 650 mg of styrene/g.

The particle size of the styrene-hypophosphite adduct aluminum salt is preferably from 0.1, to 1000 µm, the proportion of the $R_9$ side chains deriving from the initiator is preferably below 40%, and the styrene binding power is preferably from 260 to 810 mg of styrene/g.

The particle size of the styrene-hypophosphite adduct aluminum salt is particularly preferably from 10 to 100 µm, the proportion of the $R_9$ side chains deriving from the initiator is particularly preferably below 18%, and the styrene binding power is particularly preferably from 360 to 650 mg of styrene/g.

The particle size of the styrene-hypophosphite adduct zinc salt is preferably from 0.1 to 1000 µm, the proportion of the $R_9$ side chains deriving from the initiator is preferably below 40%, and the styrene binding power is preferably from 190 to 650 mg of styrene/g.

The particle size of the styrene-hypophosphite adduct zinc salt is particularly preferably from 10 to 100 µm, the proportion of the $R_9$ side chains deriving from the initiator is particularly preferably below 18%, and the styrene binding power is particularly preferably from 240 to 570 mg of styrene/g.

Crude polystyrene may comprise from 10 to 100 ppm of styrene monomer resulting from the synthesis. Surprisingly, it has now been found that the styrene-hypophosphite adduct can effectively immobilize styrene monomer if it is added to the polystyrene during the processing of the plastic.

According to the invention, the styrene binding power of the styrene-hypophosphite adduct is from 260 to 810% by weight, preferably from 360 to 650% by weight.

According to the invention, the styrene binding power of the aluminum salt of the styrene-hypophosphite adduct is from 260 to 810% by weight, preferably from 360 to 650% by weight.

According to the invention, the styrene binding power of the zinc salt of the styrene-hypophosphite adduct is from 190 to 650% by weight, preferably from 240 to 570% by weight.

The invention also provides a process for preparing styrene-hypophosphite adducts, which comprises using a phosphorus-containing compound and a styrene-containing compound as an initial charge, and causing these to react through uniform feed of a free-radical initiator.

Another embodiment of the process for preparing styrene-hypophosphite adducts is one wherein a phosphorus-containing compound is used to form an initial charge, and is caused to react through uniform and simultaneous feed of a free-radical initiator and a styrene-containing compound.

As an alternative, a phosphorus-containing compound and a styrene-containing compound may be used as an initial charge in a solvent and caused to react, and a free-radical initiator may be fed uniformly, directly or in a solvent, in the course of the reaction.

The molar ratio of phosphorus-containing compound to styrene-containing compound and, respectively, to the solvent is preferably from 1:1 to 1:100.

The molar ratio of phosphorus-containing compound to styrene-containing compound and, respectively, to the solvent is particularly preferably from 1:1 to 1:10.

According to the invention, from 0.001 to 10 mol % of free-radical initiator is fed per hour (based on the starting phosphorus component).

The amounts used of the free-radical initiator are particularly preferably from 0.01 to 10 mol %, based on the phosphorus-containing compound.

The phosphorus-containing compound preferably comprises phosphorus hydride, hypophosphorous acid, phosphorous acid, hypodiphosphorous acid, pyrophosphorous acid, diphosphorous acid, and/or their salts, esters, and compounds containing halogen or containing other hetero atoms.

The phosphorus-containing compounds are preferably present in the form of their alkali metal salts.

The phosphorus-containing compound is preferably sodium hypophosphite.

It is preferable to feed from 0.001 to 10 mol % of initiator per hour, based on the phosphorus-containing compound.

A preferred method for the inventive process is one wherein the initial charge used comprises sodium hypophosphite in a mixture composed of a solvent and a mineral acid, and this charge is heated to reaction temperature, and free-radical initiator and styrene component are uniformly fed during a period of from 2 to 10 h, and then the product is cooled and worked up in order to obtain the sodium salt of the styrene-hypophosphite adduct.

An alternative method for the inventive process is one wherein the initial charge used comprises sodium hypophosphite in water and/or acetic acid, and this charge is heated to reaction temperature, and free-radical initiator and styrene component are uniformly fed during a period of from 2 to 10 h in at least one solvent, and then the product is cooled and worked up in order to obtain the sodium salt of the styrene-hypophosphite adduct.

The invention also provides a phosphorus-containing flame retardant, comprising the inventive styrene-hypophosphite adduct.

The phosphorus-containing flame retardant preferably comprises from 50 to 99% by weight of styrene-hypophosphite adduct and from 1 to 50% by weight of one or more additives.

The additive is preferably nitrogen compounds of the formulae (III) to (VIII), or a mixture of these.

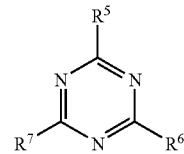

(III)

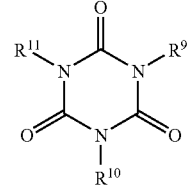

(IV)

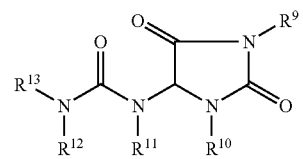

(V)

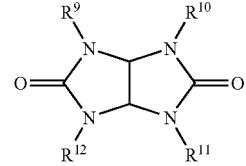

(VI)

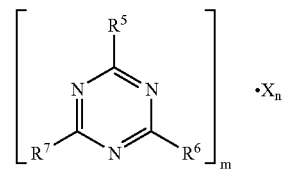

(VII)

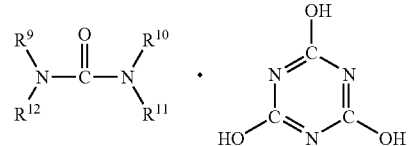

(VIII)

where
$R^5$ to $R^7$ are hydrogen, $C_1$–$C_8$-alkyl, $C_5$–$C_{16}$-cycloalkyl, or -alkylcycloalkyl, where appropriate substituted with a hydroxy function or with a $C_1$–$C_4$-hydroxyalkyl function, $C_2$–$C_8$-alkenyl, $C_1$–$C_8$-alkoxy, -acyl, -acyloxy, $C_6$–$C_{12}$-aryl or -arylalkyl, —$OR^8$, or —$N(R^8)R^9$, or else a system of N-alicyclic or N-aromatic nature, $R^8$ is hydrogen, $C_1$–$C_8$-alkyl, $C_5$–$C_{16}$-cycloalkyl or -alkylcycloalkyl, where appropriate substituted with a hydroxy or a $C_1$–$C_4$-hydroxyalkyl function, $C_2$–$C_8$-alkenyl, $C_1$–$C_8$-alkoxy, -acyl, -acyloxy, or $C_6$–$C_{12}$-aryl or -arylalkyl, $R^9$ to $R^{13}$ are the same as the groups for $R^8$, or else —O—$R^8$, m and n, independently of one another, are 1, 2, 3 or 4, X is acids which can form adducts with triazine compounds (III).

The additive is particularly preferably melamine phosphate, dimelamine phosphate, melamine pyrophosphate, melamine polyphosphates, melam polyphosphates, melem polyphosphates, and/or melon polyphosphates; melamine condensates, such as melam, melem and/or melon; oligomeric esters of tris(hydroxyethyl) isocyanurate with aromatic polycarboxylic acids, benzoguanamine, tris(hydroxyethyl) isocyanurate, allantoin, glycoluril, melamine, melamine cyanurate, dicyandiamide, and/or guanidine; nitrogen-containing phosphates of the formulae $(NH_4)_y H_{3-y}PO_4$ or $(NH_4 PO_3)_z$, where y is from 1 to 3 and z is from 1 to 10,000; a synthetic inorganic compound, and/or a mineral product.

The particle size of the phosphorus-containing flame retardant is preferably from 0.1 to 2000 μm, and its residual moisture level is preferably from 0.01 to 10% by weight.

The particle size of the phosphorus-containing flame retardant is particularly preferably from 10 to 200 μm, and its residual moisture level is particularly preferably from 0.05 to 1% by weight.

The invention also provides powder molding compositions, comprising from 1 to 50% by weight of the phosphorus-containing flame retardant from 1 to 99% by weight of polystyrene-based polymer or a mixture of the same from 0 to 60% by weight of additives from 0 to 60% by weight of filler.

The invention also provides polymer moldings, polymer films, polymer filaments, and polymer fibers, comprising from 1 to 50% by weight of the phosphorus-containing flame retardant from 1 to 99% by weight of polystyrene-based polymer or a mixture of the same from 0 to 60% by weight of additives from 0 to 60% by weight of filler.

The invention also provides an intumescent flame-retardant coating comprising from 1 to 50% by weight of the phosphorus-containing flame retardant from 0 to 60% by weight of ammonium polyphosphate and also from 0 to 80% by weight of binder, foamers, fillers, and additives.

Process for Preparing the Styrene-Hypophosphite Adduct

Phosphorus Starting Component

According to the invention, use may be made of any of the phosphorus compounds of which at least one tautomeric form has at least one P—H group. Preference is given to phosphorus hydride, hypophosphorous acid, phosphorous acid, hypodiphosphorous acid, pyrophosphorous acid, diphosphorous acid, and/or their salts, esters, and compounds containing halogen or containing other hetero atoms. The alkali metal salts are preferred, and the sodium salts are very particularly preferred.

Styrene Starting Component

Preference is given to styrene; alkylstyrene, such as p-methylstyrene, p-ethylstyrene, p-propylstyrene, p-isopropylstyrene, p-butylstyrene, p-tert-butylstyrene, p-phenylstyrene, o-methylstyrene, o-ethylstyrene, o-propylstyrene, o-isopropylstyrene, m-methylstyrene, m-ethylstyrene, m-isopropylstyrene, m-butylstyrene, mesitylstyrene, 2,4-dimethylstyrene, 2,5-dimethylstyrene, 3,5-dimethylstyrene, etc.; hydroxystyrenes, such as o-hydroxystyrene, p-hydroxystyrene and m-hydroxystyrene; alkoxystyrenes, such as o-, m-, p-methoxystyrene, o-, m-, p-ethoxystyrene, 4-methoxy-3-methylstyrene, p-propoxystyrene, p-phenoxystyrene, p-tert-butoxystyrene, p-trityloxystyrene, etc.; siloxystyrenes such as p-trimethylsiloxystyrenes, p-tert-butyldimethylsiloxystyrenes, p-triisopropylsiloxystyrenes; halostyrenes, such as o-, m-, p-chlorostyrene, o-, m-, p-bromostyrene, o-, m-, p-fluorostyrene, o-methyl-p-fluorostyrene, etc.; and also trimethylsilylstyrene, vinyl benzoates, divinylbenzene, etc.

Preference is given to p-acetoxystyrenes; ether styrenes, such as p-vinylbenzyl methyl ether, p-vinylbenzyl ethyl ether, p-vinylbenzyl n-propyl ether, p-vinylbenzyl isopropyl ether, p-vinylbenzyl n-butyl ether, p-vinylbenzyl tert-butyl ether, 1-(4-vinylphenyl)-1,1-dimethylmethyl methyl ether, 1-(4-vinylphenyl)-1,1-dimethylmethyl ethyl ether, 1-(4-vinylphenyl)-1,1-dimethylmethyl propyl ether, 1-(4-vinylphenyl)-1,1-dimethylmethyl butyl ether, 1-(4-vinylphenyl)-1,1-diphenylmethyl methyl ether, 1-(4-vinylphenyl)-1,1-diphenylmethyl ethyl ether, 1-(4-vinylphenyl)-1,1-diphenylmethyl butyl ether, 1-(4-vinylphenyl)-1,1-dimethylmethyl trimethylsilyl ether, and 1-(4-vinylphenyl)-1,1-dimethylmethyl triethylsilyl ether; alcohols such as p-vinylbenzyl alcohol, (4-vinylphenyl)-1,1-dimethylmethanol, (4-vinylphenyl)-1,1-diphenylmethanol, and 2-(4-vinylphenyl)ethanol; amines, such as 2-aminostyrene, 3-aminostyrene, 4-aminostyrene, 3,4-diaminostyrene, 4-vinylbenzylamine, and 2-(4-vinylphenyl)ethylamine; alkyl-substituted aminostyrenes, such as m-N,N-dimethylaminostyrene, p-N,N-dimethylaminostyrene, p-vinylbenzyl-N,N-dimethylamine, p-vinylbenzyl-N,N-diethylamine, p-vinylbenzyl-N,N-di-n-propylamine, p-vinylbenzyl-N,N-d i-n-butylamine, p-(N,N-dimethylamino)styrene, p-(N,N-diethylamino)styrene, p-(N,N-di-n-propylamino)styrene, p-(N,N-d i-n-butylamino)styrene, N-(p-vinylbenzyl)pyrrolidine, N-(p-vinylbenzyl)piperidine, and N-(p-vinylbenzyl)morpholine; styrenes having carbonyl groups, such as p-vinylbenzoic acid, methyl p-vinylbenzoate, phenyl p-vinylbenzoate, methyl 3-vinylsalicylate, p-formylstyrene, p-acetylstyrene, and p-vinylbenzophenone; cyanostyrenes, such as o-, m-, p-cyanostyrenes; mercaptostyrenes and alkylthiostyrenes, such as o-, m-, p-mercaptostyrenes, o-, m-, p-methylthiostyrenes, o-, m-, p-ethylthiostyrene; p-styryldiphenylphosphine; 3,5-dimethyl-4-hydroxystyrenes; 3,5-diethyl-4-hydroxystyrene; 3,5-dipropyl-4-hydroxystyrene; 3,5-diisopropyl-4-hydroxystyrene; 3,5-di-tert-butyl-4-hydroxystyrene; 3,5-di-tert-butyl-4-aminostyrene, and 3,5-di-tert-butylcarboxystyrene.

Particular preference is given to styrene, alkylstyrenes, and divinylbenzene. Styrene, alpha-methylstyrene, p-methylstyrene and divinylbenzene are particularly preferred.

Preference is also given to styrene-phenol polyethylene glycol ethers, e.g. Emulsogen$^R$ TS grades (e.g. TS160, TS200, TS290, TS540) from Clariant GmbH.

According to the invention, (co)polymerization may have been carried out using one or more types of the abovementioned styrenes in any desired configuration.

Initiator

The oligomeric phosphonous acid-styrene adduct may be prepared in a slurry process, a solution process, an emulsion process, or a bulk process.

The reaction of the styrene to form the adduct may be initiated by an anionic initiator, by a free-radical initiator, or photochemically.

Surprisingly, it has now been found that the phosphorus yield can be raised over the level described in the prior art if the initiator is metered slowly and uniformly, at low metering rates, into the phosphorus starting component. The form in which the initiator is separately metered here may be pure, or dissolved in a solvent. In another embodiment, the form in which the initiator is fed is a styrene solution, or a mixture with styrene dissolved in a solvent.

In principle, suitable systems for the process are any of those which generate free radicals. Particular preference is given to peroxo compounds, such as potassium persulfate, sodium persulfate, ammonium persulfate, benzoyl peroxide, hydrogen peroxide, di-tert-butyl peroxide, dicumyl peroxide, 2,4-dichlorobenzoyl peroxide, decanoyl peroxide, lauroyl peroxide, cumene hydroperoxide, pinene hydroperoxide, p-menthane hydroperoxide, tert-butyl hydroperoxide, acetylacetone peroxide, methyl ethyl ketone peroxide, peroxosuccinic acid, dicetyl peroxydicarbonate, tert-butyl peroxyacetate, tert-butyl peroxymaleate, tert-butyl peroxybenzoate, acetylcyclohexylsulfonyl peroxide.

Other preferred initiators are azoinitiators, such as 2-tert-butylazo-2-cyanopropane, dimethyl azodiisobutyrate, azodiisobutyronitrile, 2-tert-butylazo-1-cyanocyclohexane, 1-tert-amylazo-1-cyanocyclohexane. Other preferred compounds are alkyl perketals, such as 2,2-bis-(tert-butylperoxy)butane, ethyl 3,3-bis(tert-butylperoxy)butyrate, 1,1-di-(tert-butylperoxy)cyclohexane.

Particular preference is given to VAZO 52, VAZO 64 (AIBN), VAZO 67, VAZO 88, VAZO 44, VAZO 56, VAZO 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis(2-methylbutyronitrile), V-40, VF-096 1,1'-azobis(cyclohexane-1-carbonitrile), V-30 1-[(cyano-1-methylethyl)azo]-formamide, VAm-110 2,2'-azobis(N-butyl-2-methylpropionamide), VAm-111 2,2'-azobis(N-cyclohexyl-2-methylpropionamide) VA-041 2,2'-azobis[2-(5-methyl-2-imidazolin-2-yl)propane]dihydrochloride, VA-044 2,2'-azobis[2-(2-imidazolin-2-yl)propane]dihydrochloride, VA-046B 2,2'-azobis[2-(2-imidazolin-2-yl)propane disulfate dihydrate, V-50 2,2'-azobis(2-amidinopropane) hydrochloride, VA-057 2,2'-azobis[N-(2-carboxyethyl)-2-methylpropionamidine]tetrahydrate, VA-058 2,2'-azobis[2-(3,4,5,6-tetrahydropyrimidin-2-yl)propane]dihydrochloride, VA-060 2,2'-azobis{2-[1-(2-hydroxyethyl)-2-imidazolin-2-yl]propane} dihydrochloride, VA-061 2,2'-azobis[2-(2-imidazolin-2-yl)propane], VA-080 2,2'-azobis{2-methyl-N-[1,1-bis(hydroxymethyl)-2-hydroxyethyl]propionamide, VA-085 2,2'-azobis{2-methyl-N-[2-(1-hydroxybutyl)]propionamide}, VA-086 2,2'-azobis[2-methyl-N-(2-hydroxyethyl)propionamide] from Wako Chemicals.

A solvent may be used for the preparation. Preference is given to water, alcohols, e.g. methanol, n-propyl alcohol, isopropyl alcohol, n-butanol, isobutanol, amyl alcohol, etc. Preference is also given to aliphatic hydrocarbons, such as hexane, heptane, octane, and petroleum ether; aromatic hydrocarbons, such as benzene, toluene, xylene, ethylbenzene, diethylbenzene and chlorobenzene; halogenated hydrocarbons, such as methylene chloride, chloroform, 1,2-dichloroethane, chlorobenzene, etc., carbon tetrachloride, tetrabromoethylene; alicyclic hydrocarbons, such as cyclopentane, cyclohexane, and methylcyclohexane; ketones, such as diisobutyl ketone and methyl n-propyl ketone; esters, such as n-propyl acetate and n-butyl acetate, etc. Sole use or combined use may be made of one or more of these compounds.

Particular preference is given to the exclusive use of water as solvent or dispersion medium. By way of example, if alcohols, such as butanol etc., are used as cosolvents or codispersants, the amounts of these used are subordinate, i.e. their content in the solvent system is less than 50%. According to the invention, this can inhibit the disproportionation of the hypophosphite.

The pressure may vary from atmospheric pressure to 196 MPa. The temperature may vary from 50 to 150° C.

Emulsifying Agents

It is advantageous to use an emulsifying agent, e.g. anionic surfactants, such as sodium rosinate, potassium stearate, sodium oleate, sodium laurate, and sodium dodecylbenzenesulfonate; cationic surfactants, such as cetyltrimethylammonium bromide and dodecylamine chloride; non-ionic surfactants, such as nonyl polyoxyethylene ethers and octylphenyl polyoxyethylene ethers, etc. These emulsifying agents may be used alone or in a mixture with one another.

According to the invention, use is made of from 0.01 to 10% of emulsifier, based on the amount of phosphorus used, preferably from 0.1 to 1% of emulsifier.

Ratios of Materials

According to the invention, phosphorus starting component and styrene are used to form an initial charge in a solvent. The molar ratio of phosphorus starting component to styrene is preferably from 1:1 to 1 100, particularly preferably from 1:1 to 1:10, with particular preference from 1:1 to 1:3. The molar ratio of phosphorus starting component to solvent is preferably from 1:1 to 1:100, particularly preferably from 1:1 to 1:10. The free-radical initiator is preferably metered slowly into the mixture. According to the invention, the amounts used of the initiators are from 0.01 to 10 mol %, based on the phosphorus starting component.

In a preferred method, the phosphorus starting component is used to form an initial charge in a solvent. The molar ratio of phosphorus starting component to solvent is preferably from 1:1 to 1:100, particularly preferably from 1:1 to 1:10. The free-radical initiator is preferably metered slowly in a mixture with the styrene into the phosphorus starting component. The molar ratio of phosphorus starting component to styrene is preferably from 1:1 to 1:100, particularly preferably from 1:1 to 1:10, with particular preference from 1:1 to 1:3. According to the invention, the amounts used of the initiators are from 0.01 to 10 mol %, based on the phosphorus starting component.

In a preferred method, the phosphorus starting component is used to form an initial charge in a solvent. The molar ratio of phosphorus starting component to solvent is preferably from 1:1 to 1:100, particularly preferably from 1:1 to 1:10. The free-radical initiator and the styrene are preferably metered slowly into the phosphorus starting component. The molar ratio of phosphorus starting component to styrene is preferably from 1:1 to 1:100, particularly preferably from 1:1 to 1:10, with particular preference from 1:1 to 1:3.

According to the invention, the amounts used of the initiators are from 0.01 to 10 mol %, based on the phosphorus starting component.

The reaction solution may be acidified in order to prepare the acid form of the styrene-hypophosphite adduct. The pH range from 0 to 6 is preferred, in particular from 0.5 to 3. However, the acidification of the reaction solution may also be delayed until the styrene-addition reaction has finished.

Preferred suitable acidic components are mineral acids, such as hydrochloric acid, sulfuric acid, phosphoric acid.

Preference is also given to carboxylic acids, such as formic acid, acetic acid, oxalic acid.

A particularly preferred method carries out the reaction in glacial acetic acid.

A particularly preferred method carries out the reaction in aqueous solution. The pH range from 3 to 7 is then preferred.

In another embodiment, the addition of acid is omitted, and the pH of the reaction solution is then preferably from 4 to 10, particularly preferably from 5 to 8.

If no acid is added, the styrene adduct is produced in the form of a salt. The solution of the salt may then serve as starting product for the preparation of salts with other cations. Preference is given to $Li^+$, $Na^+$, $K^+$, $Ca^{2+}$, $Mg^{2+}$, $Sr^{2+}$, $Ba^{2+}$, $Zn^{2+}$, $Sn^{2+}$, $Al^{3+}$, $Bi^{3+}$, $Fe^{2+}$, $Fe^{3+}$, $Mn^{2+}$, $Mn^{3+}$, $Ce^{3+}$, $Ti^{4+}$, $TiO^{2+}$, $Zr^{4+}$, $ZrO^{2+}$, and organic nitrogen cations, such as the parent structures and derivatives of ammonia, of melamine, of guanidine, of mono-, di-, or triethanolamine, of piperazine, of triethylamine, of ethylenediamine, and of urea.

The salts of the styrene-hypophosphite adduct are prepared by methods based on those in the applications DE 197 52 735 A1 and DE 19851 729 A1.

To this end, the solution of the styrene adduct is reacted with a solution of a salt of the desired cation. Preference is given to the respective highly water-soluble halides, oxo-halogen acids, oxo-sulfur acids (e.g. sulfates), oxo-boron acids (e.g. borates), oxo-nitrogen acids (e.g. nitrates). Water-solubility is preferably above 20%, particularly preferably above 50%.

The reaction preferably takes place from aqueous solution, taking the form of a precipitation or crystallization. The pH of the precipitation solution is preferably from 1 to 10, very particularly preferably from 3 to 8. The temperature is from 0 to 250° C., preferably from 10 to 150° C.

The relevant cations may also be used by way of their oxides, hydroxides, or oxide hydroxides. In this case, preference is given to hydrothermal crystallization conditions using temperatures of from 90 to 250° C. and using the corresponding autogenic solvent pressure.

In another preferred method, the styrene-hypophosphite adduct is converted into the acid form and is reacted with the corresponding elemental metals. This is particularly preferred in the case of metallic aluminum. The styrene adduct may preferably be converted into the acidic form through treatment with an acidic cation exchanger.

The flame retardant may itself be added to an emulsion intended for styrene polymerization and be incorporated into the polymer by reaction.

Phosphorus-Containing Flame Retardants

The invention also provides the use of the styrene-hypophosphite adduct in phosphorus-containing flame retardants. Surprisingly, it has been found that the styrene-hypophosphite adduct may be used in phosphorus-containing flame retardants. Preference is given to flame retardants comprising from 50 to 99% by weight of styrene-hypophosphite adduct and from 1 to 50% by weight of other-additives, e.g. synergists (as described in DE 196 14 424 A1 and DE 199 60 671 A1), pelletizing auxiliaries, e.g. waxes, polyamide copolymers, such as ®Vestamelt 730-P1 from Degussa, polyester copolymers, such as ®Vestamelt 4481-P1 and 4680-P1 from Degussa, and ®Griltex 1582E P1 and 1365E P1 from Ems-Griltex), dust-reducing agents, e.g. dioctyl phthalate (DOP), silicone oils, mineral oils, glycerol, glycol, etc.), and compacting auxiliaries.

The additive may be a synthetic inorganic compound and/or a mineral product. Suitable materials are oxygen compounds of silicon, magnesium compounds, metal carbonates of metals of the second main group of the Periodic Table of the Elements, red phosphorus, zinc compounds, or aluminum compounds.

The oxygen compounds of silicon are preferably salts and esters of orthosilicic acid and condensates thereof, silicates, zeolites, and silicas, glass powders, glass/ceramic powders, or ceramic powders; the magnesium compounds are preferably magnesium hydroxide, hydrotalcites, magnesium carbonates, or magnesium calcium carbonates; the zinc compounds are preferably zinc oxide, zinc stannate, zinc hydroxystannate, zinc phosphate, zinc borate, or zinc sulfides; the aluminum compounds are preferably aluminum hydroxide or aluminum phosphate.

Preparation of the Phosphorus-containing Flame Retardant

The inventive phosphorus-containing flame retardant may be prepared in an embodiment which adds further additive in liquid form, in a suitable mixer, to the moving solid styrene-hypophosphite adduct, and mixes for from 0.1 to 100 hours at from 20 to 200° C., and then, where appropriate, dries the material at from 20 to 400° C. Further additives which are solid at ambient temperature are then applied in molten form to the material.

In another embodiment, the inventive phosphorus-containing flame retardant may be prepared by adding the further solid additive, in a suitable mixer, to the moving solid styrene-hypophosphite adduct, mixing for from 0.1 to 100 hours, and, during this process, heating to the melting point of the further additive. Suitable temperatures are from 20 to 200° C.

Suitable mixers may be: plowshare mixers from Lödige, rotating-disk mixers from Lödige, (e.g. CB30), Flexomix mixers from Schugi, HEC rotating-disk mixers from Niro, rotating-disk mixers from Drais, Mannheim, Eirich mixers (e.g. R02), Henschel mixers, Papenburg mixers, Telschig mixers (WPA6), zig-zag mixers from Niro.

The product mixture initially produced can be dried in a suitable dryer, or heat-treated to enlarge the particles. Dryers of the invention may be: fluidized-bed dryers from Hosokawa Schugi (Schugi Fluid-Bed, Vometec fluidized-bed dryers), fluidized-bed dryers from Waidner or from Glatt, turbo-fluidized-bed dryers from Waldner, spin-flash dryers from Anhydro, or else drum dryers.

Preferred operating conditions in the fluidized-bed dryer are: air inlet temperature from 120–280° C., product temperature from 20 to 200° C.

The particle size of the phosphorus-containing flame retardant is preferably from 0.1 to 2000 μm, particularly preferably from 10 to 200 μm.

The residual moisture level in the inventive phosphorus-containing flame retardant is from 0.01 to 10%, preferably from 0.05 to 1%.

The flowability of the inventive phosphorus-containing flame retardant, determined by a method based on DIN 53916, and expressed as the cotangent of the angle of repose Phi, is preferably from 1 to 2, particularly preferably from 1.2 to 1.8. The flowability was determined using the PFRENGLE test equipment stated in DIN 53 916. (DIN 53 916 (August 1974 issue): Determination of flowability of powders and granular materials.)

The tendency of the inventive phosphorus-containing flame retardant toward dusting is quantified at from 1 to 65%, preferably from 5 to 60%. 10 g of the material to be studied are weighed into a wash bottle. Nitrogen is passed for 20 min through the material, the gas flow rate being 1 l/min. The amount of powder then remaining is weighed. The proportion discharged is divided by the initial weight, and related to 100%.

Polymer Molding Compositions

The invention further provides flame-retardant polymer molding compositions.

The flame-retardant polymer molding composition preferably comprises
from 1 to 50% by weight of phosphorus-containing flame retardant
from 1 to 99% by weight of polystyrene-based polymer
from 0 to 60% by weight of additives
from 0 to 60% by weight of filler.

The flame-retardant polymer molding composition particularly preferably comprises from 5 to 30% by weight of phosphorus-containing flame retardant
from 5 to 90% by weight of polystyrene-based polymer
from 5 to 40% by weight of additives
from 5 to 40% by weight of filler.

Polystyrene-based Polymer

Preferred application for the inventive phosphorus-containing flame retardant is the use as flame retardant in polymers. Particular preference is given to vinylaromatic homo- and copolymers based on styrene, chlorostyrene, alpha-methylstyrene and p-methylstyrene. The molecular weight of these polymers, which are known and commercially available, is generally in the range from 1500 to 2000000, preferably in the range from 50000 to 1000000. Subordinate proportions (preferably not more than 20% by weight, in particular not more than 8% by weight) of comonomers, such as methacrylonitrile or (meth)acrylic esters may also be present in the structure. Particularly preferred vinylaromatic polymers are polystyrene and impact-modified polystyrene. Preference is given to styrene-acrylonitrile (SAN copolymers, e.g. as described in DE 199 20 276 A1), alpha-methylstyrene-acrylonitrile copolymers, styrene-methyl methacrylate copolymers, styrene-maleic anhydride copolymers, styrene-maleimide copolymers, styrene-acrylate copolymers, acrylonitrile-butadiene-styrene (ABS) polymers, and blends. Preference is also given to graft polymers, e.g. as described in DE 199 20 276 A1.

Commercially available grades are polystyrene (BASF), Lacqrene (Atofina), Styron (Dow) etc.

Polymer Moldings

Finally, the invention also provides polymer moldings, polymer films, polymer filaments, and polymer fibers, comprising the inventive granular flame retardant composition.

The polymer moldings, polymer films, polymer filaments, and polymer fibers preferably comprise
from 1 to 50% by weight of phosphorus-containing flame retardant
from 1 to 99% by weight of polystyrene-based polymer or a mixture of the same
from 0 to 60% by weight of additives
from 0 to 60% by weight of filler.

The polymer moldings, polymer films, polymer filaments, and polymer fibers particularly preferably comprise
from 5 to 30% by weight of phosphorus-containing flame retardant
from 5 to 90% by weight of polystyrene-based polymer or a mixture of the same
from 5 to 40% by weight of additives
from 5 to 40% by weight of filler.

It is also possible to mix the flame-retardant additives with ready-to-use polymer pellets or ready-to-use polymer powder, and to process the mixture directly in an injection-molding machine, to give moldings.

Preferred fillers are glass (preferably in bead or fiber form), oxides and/or hydroxides of the elements of the second and third main group of the Periodic Table of the Elements (preferably aluminum and magnesium), phyllosilicates, and clay minerals, e.g. bentonites, montmorillonites, hectorites, saponites, precipitated/fumed/crystalline/amorphous silicas, chalk.

Preferred additives are synergists, antioxidants, light stabilizers, lubricants, colorants, nucleating agents, or antistatic agents. Examples of the additives which can be used are stated in EP 0 584 567 A1.

EXAMPLE 1 (COMP.)

53 g (0.5 mol) of sodium hypophosphite monohydrate, 15.6 g (0.15 mol) of styrene, and 2.3 g of AIBN (VAZO 64, Dupont-Biesteritz) are used to form an initial charge, with stirring, in a mixture of 243 g of ethanol and 24 g of concentrated sulfuric acid. The reaction solution is heated at reflux (about 78° C.) for 6 h. A further 1.6 g of AIBN are then added, and the mixture is heated to boiling for a further 12 h. After cooling, the solution is filtered and concentrated by evaporation to dryness. The residue is taken up in 100 g of water and extracted with 100 g of ethyl acetate, and the extract is concentrated by evaporation to dryness. This gives 14.3 g of product with a P content of 7.5% by weight (6.9% P yield).

EXAMPLE 2

53 g (0.5 mol) of sodium hypophosphite monohydrate, and 51.9 g (0.5 mol) of styrene are used to form an initial charge, with stirring, in a mixture of 193 g of ethanol and 24 g of concentrated sulfuric acid. 3.9 g of AIBN (VAZO 64, Dupont-Biesteritz) dissolved in 50 g of ethanol are fed, using a pump, while the reaction solution is heated to reflux (about 78° C.) for 5 h. The reaction solution is worked up as in Example 1. This gives 63.8 g of product with a P content of 15.7% by weight (64.7% P yield).

EXAMPLE 3

53 g (0.5 mol) of sodium hypophosphite monohydrate are used to form an initial charge, with stirring, in a mixture of 243 g of ethanol and 24 g of concentrated sulfuric acid. 3.9 g of AIBN (VAZO 64, Dupont-Biesteritz) and 51.9 g (0.5 mol) of styrene are fed, using a pump, while the reaction solution is heated to reflux (about 78° C.) for 5 h. The reaction solution is worked up as in Example 1. This gives 73.4 g of product with a P content of 18.9% by weight (89.6% P yield).

EXAMPLE 4

26.5 g (0.25 mol) of sodium hypophosphite monohydrate are used to form an initial charge, with stirring, in a mixture of 243 g of ethanol and 24 g of concentrated sulfuric acid. 3.9 g of AIBN (VAZO 64, Dupont-Biesteritz) and 51.9 g (0.5 mol) of styrene are fed, using a pump, while the reaction solution is heated to reflux (about 78° C.) for 5 h. The reaction solution is worked up as in Example 1. This gives 59.2 g of product with a P content of 10.2% by weight (78.0% P yield).

EXAMPLE 5

26.5 g (0.25 mol) of sodium hypophosphite monohydrate are used to form an initial charge, with stirring. in a mixture of 160 g of ethanol, 80 g of water, and 24 g of concentrated sulfuric acid. 3.9 g of AIBN (VAZO 64, Dupont-Biesteritz) and 51.9 g (0.5 mol) of styrene are fed, using a pump, while the reaction solution is heated to reflux (about 78° C.) for 5 h. The reaction solution is worked up as in Example 1. This gives 64.9 g of product with a P content of 11.5% by weight (96.4% P yield).

EXAMPLE 6

5.3 g (0.05 mol) of sodium hypophosphite monohydrate are used to form an initial charge, with stirring, in a mixture of 243 g of ethanol and 24 g of concentrated sulfuric acid. 3.9 g of AIBN (VAZO 64, Dupont-Biesteritz) and 51.9 g (0.5 mol) of styrene are fed, using a pump, while the reaction solution is heated to reflux (about 78° C.) for 10 h. The reaction solution is worked up as in Example 1. This gives 49.7 g of product with a P content of 2.7% by weight (86.6% P yield).

EXAMPLE 7

53 g (0.5 mol) of sodium hypophosphite monohydrate are used to form an initial charge, with stirring, in a mixture of 243 g of ethanol and 24 g of concentrated phosphoric acid. 3.9 g of AIBN (VAZO 64, Dupont-Biesteritz) and 51.9 g (0.5 mol) of styrene are fed, using a pump, while the reaction solution is heated to reflux (about 78° C.) for 5 h. The reaction solution is worked up as in Example 1. This gives 74.5 g of product with a P content of 17.9% by weight (86.1% P yield).

EXAMPLE 8

26.5 g (0.25 mol) of sodium hypophosphite monohydrate are used to form an initial charge, with stirring, in 100 g of water. 2.9 g of sodium persulfate (itself dissolved in 50 g of water) and 51.9 g (0.5 mol) of styrene are fed, in each case using a pump, while the reaction solution is heated to about 95° C. for 5 h. The reaction solution is acidified using 24 g of concentrated sulfuric acid, and worked up as in Example 1. This gives 59.8 g of product with a P content of 10.0% by weight (77.0% P yield).

EXAMPLE 9

39.8 g (0.38 mol) of sodium hypophosphite monohydrate are used to form an initial charge, with stirring, in a mixture of 100 g of water and 1.8 g of sodium lauryl sulfate. 0.4 g of sodium persulfate (itself dissolved in 50 g of water) and 58.9 g (0.5 mol) of alpha-methylstyrene are fed, in each case using a pump, while the reaction solution is heated to about 95° C. for 5 h. The reaction solution is treated with 34.39 g of an aqueous aluminum sulfate solution (4.3% of aluminum). The precipitated product is filtered off, washed with 200 g of demin. water, and dried at 120° C. for 5 h. This gives 82.32 g of product with a P content of 12.37% by weight (86.5% P yield).

EXAMPLE 10

Al Salt 53 g (0.5 mol) of sodium hypophosphite monohydrate are used to form an initial charge, with stirring, in a mixture of 283 g of water and 1.0 g of linear sodium dodecylbenzenesulfonate. A mixture of 0.2 g of pinene hydroperoxide (44% activity level) and 51.9 g (0.5 mol) of styrene is fed, using a pump, while the reaction solution is heated to about 95° C. for 5 h. The reaction solution is treated with 42.1 g of an aqueous aluminum sulfate solution (4.3% of aluminum). The precipitated product is filtered off, washed with 200 g of demin. water, and dried at 120° C. for 5 h. This gives 81.4 g of product with a P content of 15.3% by weight (80.5% P yield).

EXAMPLE 11

Al Salt 53 g (0.5 mol) of sodium hypophosphite monohydrate are used to form an initial charge, with stirring, in 150 g of glacial acetic acid. A mixture of 0.7 g of Wako V50 (2,2'-azobis(2-amidinopropane hydrochloride, Wako Chemicals) in 25 g of glacial acetic acid and 50 g of water and, respectively, 51.9 g (0.5 mol) of styrene are fed, in each case using a pump, while the reaction solution is heated to about 95° C. for 5 h. The solvent is distilled off from the reaction solution in vacuo, and the residue is made up to a total weight of 200 g, using demin. water. The solution is treated with 46.5 g of an aqueous aluminum sulfate solution (4.3% of aluminum). The precipitated product is filtered off, washed with 200 g of demin. water, and dried at 120° C. for 5 h. This gives 83.8 g of product with a P content of 16.5% by weight (89.0% P yield).

EXAMPLE 12

19 parts of the flame retardant from Example 3 are mixed with 52 parts of polystyrene 2712 (BASF AG), and with 30 parts of glass fibers, and are incorporated in a twin-screw extruder (Leistritz LSM 30/34) at temperatures of from 250 to 300° C. The homogenized polymer extrudate is drawn off, cooled in a water bath, and then pelletized. After adequate drying, the pellets were processed in an injection-molding machine (Aarburg Allrounder) at melt temperatures of from 250 to 300° C., to give moldings. The V-0 classification is achieved in the UL 94 fire test.

EXAMPLE 13

23 parts of the flame retardant from Example 10 are mixed with 47 parts of polystyrene 2712 (BASF AG), and with 30 parts of glass fibers, and are incorporated in a twin-screw extruder (Leistritz LSM 30/34) at temperatures of from 250 to 300° C. The homogenized polymer extrudate is drawn off, cooled in a water bath, and then pelletized. After adequate drying, the pellets were processed in an injection-molding machine (Aarburg Allrounder) at melt temperatures of from 250 to 300° C., to give moldings. The V-0 classification is achieved in the UL 94 fire test.

The invention claimed is:
1. A styrene-hypophosphite adduct of the formula (I)

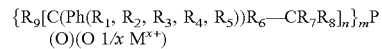

where $R_1$, $R_2$, $R_3$, $R_4$, $R_5$, $R_6$, $R_7$ and $R_8$ are identical or different and are hydrogen methyl, ethyl, n-propyl, n-butyl, n-pentyl; isopropyl, isobutyl, tert-butyl, neopentyl; phenyl; hydroxy, methoxy, ethoxy, propoxy, butoxy, phenoxy; amino, methylamino, ethylamino, propylamino, butylamino, N,N-dimethylamino, diethylamino, dipropylamino, or dibutylamino, and n is from 1 to 10, $R_9$ is H or a free-radical initiator radical, $M^{x+}$ is Li, K, Mg, Ca, Sr, Ba, Al, Ge, Sn, Bi, Sb, Pb, Ti, TiO, Zr, ZrO, Zn, Fe, Ce, Mn having the valence x, m=2, and n=from 1 to 100, and is the number of styrene units $C(Ph(R_1, R_2, R_3, R_4, R_5))R_6-CR_7R_8$ inserted into the P—H bond, said adduct being in the form of a salt.

2. The styrene-hypophosphite adduct as claimed in claim 1, wherein $R_1$, $R_2$, $R_3$, $R_4$, $R_5$, $R_6$, $R_7$, and $R_8$ are identical or different, and are hydrogen or methyl.

3. The styrene-hypophosphite adduct as claimed in claim 1, wherein said styrene-hypophosphite adduct has a phosphorus content from 8 to 25% by weight.

4. The styrene-hypophosphite adduct as claimed in claim 1, wherein said styrene-hypophosphite adduct has a phosphorus content from 11 to 20% by weight.

5. The styrene-hypophosphite adduct claimed in claim 1, wherein $M^{x+}$ is Al and said styrene-hypophosphite adduct has a phosphorus content from 8 to 25% by weight.

6. The styrene-hypophosphite adduct as claimed in claim 1, wherein $M^{x+}$ is Al and said adduct has a phosphorus content from 11 to 20% by weight.

7. The styrene-hypophosphite adduct as claimed in claim 1, wherein $M^{x+}$ is Zn and said styrene-hypophosphite adduct has a phosphorus content from 6 to 20% by weight.

8. The styrene-hypophosphite adduct as claimed in claim 1, wherein $M^{x+}$ is Zn and said styrene-hypophosphite adduct has a phosphorus content from 7.5 to 17.5% by weight.

9. The styrene-hypophosphite adduct as claimed in claim 1, wherein said styrene-hypophosphite adduct is in the form of a particle having a particle size from 0.1 to 1000 μm, the content of the side chains $R_9$ deriving from the initiator being below 40%, and said styrene-hypophosphite adduct having a styrene binding power from 260 to 810 mg of styrene/g.

10. The styrene-hypophosphite adduct as claimed in claim 1, wherein said styrene-hypophosphite adduct is in the form of a particle having a particle size from 10 to 100 μm, the content of the side chains $R_9$ deriving from the initiator being below 18%, and said styrene-hypophosphite adduct having a styrene binding power from 360 to 650 mg of styrene/g.

11. The styrene-hypophosphite adduct as claimed in claim 1, wherein $M^{x+}$ is Al, said styrene-hypophosphite adduct is in the form of a particle having a particle size from 0.1 to 1000 μm, the content of the side chains $R_9$ deriving from the initiator being below 40%, and said styrene-hypophosphite adduct having a styrene binding power from 260 to 810 mg of styrene/g.

12. The styrene-hypophosphite adduct as claimed in claim 11, said adduct is in the form of a particle having a particle size from 10 to 100 μm, the content of the side chains $R_9$ deriving from the initiator being below 18%, and said styrene-hypophosphite adduct having a styrene binding power is from 360 to 650 mg of styrene/g.

13. The styrene-hypophosphite adduct as claimed in claim 1, wherein $M^{x+}$ is Zn, said adduct is in the form of a particle having a particle size from 0.1 to 1000 μm, the content of the side chains $R_9$ deriving from the initiator being below 40%, and said styrene-hypophosphite adduct having a styrene binding power being from 190 to 650 mg of styrene/g.

14. The styrene-hypophosphite adduct as claimed in claim 13, wherein said adduct is in the form of a particle having a particle size from 10 to 100 μm, the content of the side chains $R_9$ deriving from the initiator being below 18%, and said styrene-hypophosphite adduct having a styrene binding power from 240 to 570 mg of styrene/g.

15. A process for preparing a non-sodium metal salt of styrene-hypophosphite adduct comprising the steps of forming an initial charge, wherein the initial charge includes a phosphorus-containing compound and a styrene-containing compound, and reacting the phosphorus-containing compound and the styrene containing compound through uniform feed of a free-radical initiator to the initial charge wherein the free-radical initiator is fed in an amount per hour of from 0.001 to 10 mol%, based on the phosphorus-containing compound to provide a sodium styrene-hypophosphite adduct, and cation exchanging the sodium styrene-hypophosphite adduct with a water-soluble salt of the non-sodium metal cation selected from the group consisting of a halide, an oxo-halogen acid, a sulphate, a borate, an oxo-nitrogen acid, and mixtures thereof to provide the metal salt of styrene-hypophosphite adduct, wherein said metal is not sodium.

16. A process for preparing a cation salt of styrene-hypophosphite adduct comprising the steps of forming an initial charge, wherein the initial charge includes a phosphorus-containing compound being sodium hypophosphite and reacting the phosphorous-containing compound and a styrene containing compound by uniformly and simultaneously feeding a free-radical initiator and the styrene-containing compound to the initial charge, wherein the amount of free-radical initiator fed per hour is from 0.001 to 10 mol %, based on the phosphorus-containing compound to provide a sodium salt of styrene-hypophosphite adduct, and cation exchanging the sodium salt of styrene-hypophosphite adduct with a solution of a water-soluble salt of the cation selected from the group consisting of Li, K, Mg, Ca, Sr, Ba, Al, Ge, Sn, Bi, Sb, Pb, Ti, TiO, Zr, ZrO, Zn, Fe, Ce, and Mn to provide the cation salt of styrene-hypophosphite adduct.

17. A process for preparing a salt of a styrene-hypophosphite adduct comprising the steps of reacting a phosphorus-containing compound comprising sodium hypophosphite and a styrene-containing compound in a first solvent, and uniformly feeding a free-radical initiator during the reaction of the phosphorus-containing compound and the styrene-containing compound, wherein the amount of free-radical initiator fed per hour is from 0.001 to 10 mol %, based on the phosphorus-containing compound to provide an acid form of styrene-hypophosphite adduct, and cation exchanging the acid form of styrene-hypophosphite adduct with a metal cation selected from the group consisting of Li, K, Mg, Ca, Sr, Ba, Al, Ge, Sn, Bi, Sb, Pb, Ti, TiO, Zr, ZrO, Zn, Fe, Ce, and Mn to provide the cation salt of styrene-hypophosphite adduct, and recovering the cation salt of styrene-hypophosphite adduct.

18. The process as claimed in claim 17, wherein the molar ratio of phosphorus-containing compound to the styrene-containing compound and, to the first solvent is from 1:1 to 1:100.

19. The process as claimed in claim 17, wherein the ratio of phosphorus-containing compound to the styrene-containing compound and to the first solvent is from 1:1 to 1:10.

20. The process as claimed in claim 15, wherein the amount of the free-radical initiator is from 0.01 to 10 mol %, based on the phosphorus-containing compound.

21. The process as claimed in claim 15, wherein the phosphorus-containing compound is selected from the group consisting of phosphorus hydride, hypophosphorous acid, phosphorous acid, hypodiphosphorous acid, pyrophosphorous acid, diphosphorous acid, their salts, esters, and compounds containing halogen or other hetero atoms.

22. The process as claimed in claim 15, wherein the phosphorus-containing compound is present in the form of its alkali metal salt.

23. A process for preparing a cation salt of a styrene-hypophosphite adduct comprising the steps of mixing sodium hypophosphite in a solvent and a mineral acid to form an initial charge, heating the initial charge to reaction temperature, uniformly feeding a free-radical initiator and a styrene containing compound to the initial charge for a period of from 2 to 10 h to form a reaction product, cooling the reaction product, working up the reaction product to obtain a sodium salt of the styrene hypophosphite adduct, and cation exchanging the sodium salt of the styrene hypophosphite adduct with a water-soluble salt of a metal cation, said water soluble salt selected from the group consisting of a halide, an oxo-halogen acid, a sulphate, a borate, an oxo-nitrogen acid, and mixtures thereof, said cation selected from the group consisting of Li, K, Mg, Ca, Sr, Ba, Al, Ge, Sn, Bi, Sb, Pb, Ti, TiO, Zr, ZrO, Zn, Fe, Ce, and Mn to provide the metal salt of styrene-hypophosphite adduct.

24. A process for preparing a metal cation salt of a styrene-hypophosphite adduct comprising the steps of forming an initial charge of sodium hypophosphite and at least one of water and acetic acid, heating the initial charge to reaction temperature, uniformly feeding a free-radical initiator, a styrene containing compound component and at least one solvent to the initial charge for a period of from 2 to 10 h to form a reaction product, cooling the reaction product, working up the reaction product to obtain a sodium salt of the styrene-hypophosphite adduct, and cation exchanging the sodium salt of the styrene-hypophosphite adduct with a water soluble salt of the metal cation selected from the group consisting of Li, K, Mg, Ca, Sr, Ba, Al, Ge, Sn, Bi, Sb, Pb, Ti, TiO, Zr, ZrO, Zn, Fe, Ce, and Mn to provide the metal salt of styrene-hypophosphite adduct.

25. A phosphorus-containing flame retardant, comprising from 50 to 99% by weight of styrene-hypophosphite adduct of claim 1 and from 1 to 50% by weight of at least one additive.

26. The phosphorus-containing flame retardant as claimed in claim 25, wherein the at least one additive is a nitrogen compound of the formulae (III) to (VIII) or a mixture thereof

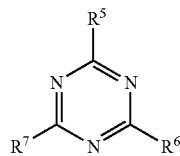

(III)

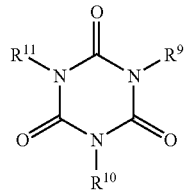

(IV)

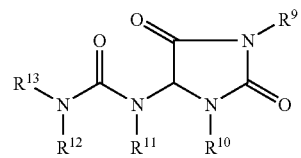

(V)

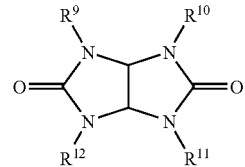

(VI)

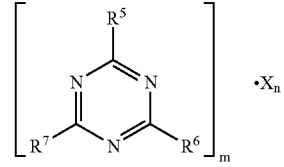

(VII)

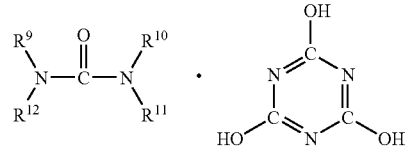

(VIII)

where
R$^5$ to R$^7$ is hydrogen, $C_1$–$C_8$-alkyl, $C_5$–$C_{16}$-cycloalkyl, or -alkylcycloalkyl, $C_2$–$C_8$-alkenyl, $C_1$–$C_8$-alkoxy, -acyl, -acyloxy, $C_6$–$C_{12}$-aryl or -arylalkyl, —OR$^8$, —N(R$^8$)R$^9$, or a system of N-alicyclic or N-aromatic nature,
R$^8$ is hydrogen, $C_1$–$C_8$-alkyl, $C_5$–$C_{16}$-cycloalkyl or -alkylcycloalkyl, $C_2$–$C_8$-alkenyl, $C_1$–$C_8$-alkoxy, -acyl, -acyloxy, or $C_6$–$C_{12}$-aryl or -arylalkyl,
R$^9$ to R$^{13}$ are the same as the groups for R$^8$, or —O—R$^8$,
m and n, independently of one another, are 1, 2, 3 or 4,
X is an acid which can form adducts with triazine compounds (III).

27. The phosphorus-containing flame retardant as claimed in claim 25, wherein the at least one additive is melamine phosphate, dimelamine phosphate, melamine pyrophosphate, melamine polyphosphates, melam polyphosphates, melem polyphosphates, melon polyphosphates; melamine condensates; oligomeric esters of tris(hydroxyethyl) isocyanurate with aromatic polycarboxylic acids, benzoguanamine, tris(hydroxyethyl) isocyanurate, allantoin, glycoluril, melamine, melamine cyanurate, dicyandiamide, guanidine; nitrogen-containing phosphates of the formulae $(NH_4)_y H_{3-y} PO_4$ or $(NH_4PO_3)_z$, where y is from 1 to 3 and z is from 1 to 10,000; a synthetic inorganic compound, or a mineral product.

28. The phosphorus-containing flame retardant as claimed in claim 25, wherein the phosphorus-containing flame retardant is in the form of a particle having a particle size of from 0.1 to 2000 μm, and a residual moisture level of from 0.01 to 10% by weight.

29. The phosphorus-containing flame retardant as claimed in claim 25, wherein the phosphorus-containing flame retardant is in the form of a particle having a particle size of from 10 to 200 μm, and a residual moisture level of from 0.05 to 1% by weight.

30. A powder molding composition, comprising from 1 to 50% by weight of the phosphorus-containing flame retardant of claim 25, from 1 to 99% by weight of polystyrene-based polymer or a mixture thereof, from 0 to 60% by weight of at least one additive, and from 0 to 60% by weight of at least one filler.

31. A polymer molding, a polymer film, a polymer filament, or a polymer fiber, comprising from 1 to 50% by weight of the phosphorus-containing flame retardant of claim 25, from 1 to 99% by weight of polystyrene-based polymer or a mixture thereof, from 0 to 60% by weight of at least one additive, and from 0 to 60% by weight of at least one filler.

32. An intumescent flame-retardant coating comprising from 1 to 50% of the phosphorus-containing flame retardant of claim 25, from 0 to 60% of ammonium polyphosphate, and from 0 to 80% by weight of at least one of binders, foamers, fillers, and additives.

33. The process as claimed in claim 17, wherein the uniformly feeding step further comprises uniformly feeding the free radical initiator in a second solvent.

34. The phosphorus-containing flame retardant as claimed in claim 26, wherein at least one of $R^5$ to $R^{13}$ is $C_1$–$C_8$-alkyl, $C_5$–$C_{16}$-cycloalkyl or -alkylcycloalkyl substituted with a hydroxy function or a $C_1$–$C_4$ hydroxyalkyl function.

35. The process of claim 17, wherein the metal cation is selected from the group consisting of aluminum, zinc, and iron.

* * * * *